United States Patent [19]

Charbonneau

[11] Patent Number: 4,661,388

[45] Date of Patent: * Apr. 28, 1987

[54] PAD FRAGRANCE SAMPLING DEVICE

[75] Inventor: Jack W. Charbonneau, Somerset, Wis.

[73] Assignee: Minnesota Mining and Manufacturing Company, St. Paul, Minn.

[*] Notice: The portion of the term of this patent subsequent to Dec. 11, 2001 has been disclaimed.

[21] Appl. No.: 695,045

[22] Filed: Jan. 24, 1985

[51] Int. Cl.$^4$ .......................... A61L 9/04; B01J 13/00; D01F 1/02; D04H 1/04
[52] U.S. Cl. ..................................... 428/43; 424/401; 424/447; 427/171; 428/321.5; 428/323; 428/327; 428/402.2; 428/402.21; 428/402.22; 428/402.24; 428/905
[58] Field of Search .............. 346/200, 226, 214, 215; 428/321.5, 905, 913, 914, 195, 201, 204, 206, 207, 323, 327, 402.2, 402.21, 402.22, 402.24, 537.5, 43; 424/27, 37; 427/171

[56] References Cited

U.S. PATENT DOCUMENTS 4,186,743 2/1980 Steiger ................................ 128/284
4,487,801 12/1984 Turnbull et al. ................. 428/313.5
4,528,226 7/1985 Sweeny ............................ 428/321.5

Primary Examiner—Bruce H. Hess
Attorney, Agent, or Firm—Donald M. Sell; James A. Smith; Mark A. Litman

[57] ABSTRACT

Microencapsulated materials are released by removing individual elements from a pad of sheets bonded by adhesive layers containing capsules.

20 Claims, 2 Drawing Figures

PAD FRAGRANCE SAMPLING DEVICE

FIELD OF THE INVENTION

This invention relates to microencapsulated materials, articles containing microencapsulated materials and the method of preparing such articles. In particular, the present invention relates to multi-element pad samples of microencapsulated materials adhesively secured in a stacked array of temporarily adhered elements such that upon breaking of the adhesion of the elements and separation of said elements, the capsules rupture, releasing or making available for application the material contained therein.

BACKGROUND OF THE INVENTION

Encapsulated materials have been used for many years in a wide variety of commercial applications. Early uses of encapsulated materials included paper coated with capsules bearing coloring material therein which could be used as a recording medium. U.S. Pat. No. 3,016,308 discloses one of the early efforts using encapsulated material as the image source on recording paper. U.S. Pat. Nos. 4,058,434 and 4,201,404 show other methods of application of encapsulated coloring materials on paper substrates to be used as imaging media and the like. U.S. Pat. No. 3,503,783 shows microcapsules having coloring material therein which are ruptureable by the application of heat, pressure and/or radiation because of a metal coating on the surface of the capsule. These ruptureable microcapsules, in one embodiment, may be secured between a substrate and a photoconductive top coat to enable photosensitive imaging of the system.

A wide variety of processes exist by which microcapsules can be manufactured. These varied processes provide different techniques for producing capsules of varying sizes, alternative materials for the composition of the capsule shell and various different functional materials within the shell. Some of these various processes are shown in U.S. Pat. Nos. 3,516,846; 3,516,941; and British Patent Specification Nos. 1,156,725; 2,041,319 and 2,048,206. A wide variety of different materials may also be used in making the capsule shells. A popular material for shell formation is the polymerization reaction product between urea and formaldehyde or melamine and formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and U.K. Patent Specification Nos. 2,006,709 and 2,062,570.

As shown in these references, the principal utility of microencapsulated materials is in the formation of a surface coated with the microcapsules in a binder. The microcapsules are ruptured by various means to release the material contained therein. In addition to release of physically observable materials such as ink in order to form a visible image, other types of active ingredients such as odor releasing materials, bacteriostatic materials, chemically active materials and the like have been provided in this manner.

U.S. Pat. No. 4,186,743 discloses a perfuming self-adhering sanitary napkin having a pressure-sensitive adhesive layer bonded to a strippable cover sheet having a binder layer with microcapsules on the surface thereof in contact with the pressure-sensitive adhesive layer. Upon stripping of the cover sheet, capsules are broken, the pressure sensitive adhesive is exposed and the napkin may adhere to undergarments to keep them properly positioned.

U.S. Pat. No. 4,487,801 discloses a fragrance releasing pull-apart sheet comprising a non-pressure-sensitive binder layer containing microcapsules adhered between two sheets. Upon separation of the sheets, the adhesive and capsules rupture, releasing the material within the capsules.

SUMMARY OF THE INVENTION

The present invention relates to a new article containing ruptureable microcapsules. The novel article comprises multiple elements usually in the form of sheets in a stacked array, the individual sheets of which are temporarily bonded by means of an adhesive with ruptureable microcapsules dispersed therein. The microcapsules are ruptured by pulling apart the sheets leaving behind the remainder of the stacked array from which additional individual sheets can be removed. The removal of individual sheets causes the capsules in the adhesive layer joining that sheet to the remainder of the stacked array to rupture and release the ingredients contained therein. The exposed or released ingredient may be applied to another surface, such as skin, by rubbing the surface of the individual sheet with ruptured capsules against another surface.

DETAILED DESCRIPTION OF THE DRAWING

Figure 1:
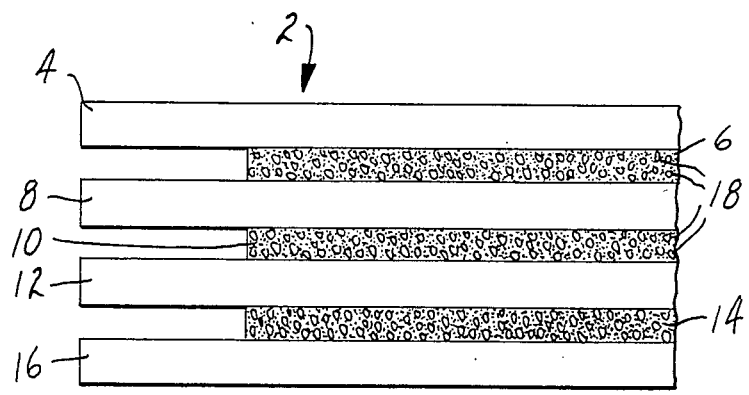
FIG. 1 shows a side view of the stacked array of elements of the present invention.

FIG. 1 shows the stacked array 2 of the present invention with a top sheet 4 adhesively secured to bottom sheet 8 by an adhesive layer 6 having ruptureable microcapsules 18 therein. The surface of the bottom sheet 8 which is away from the top sheet 4 has an adhesive layer 10 thereon securing it to the next sheet 12. That sheet 12 is further secured by adhesive layer 14 to another sheet 16. These layers will cumulatively form a pad or stacked array 2.

Figure 2:
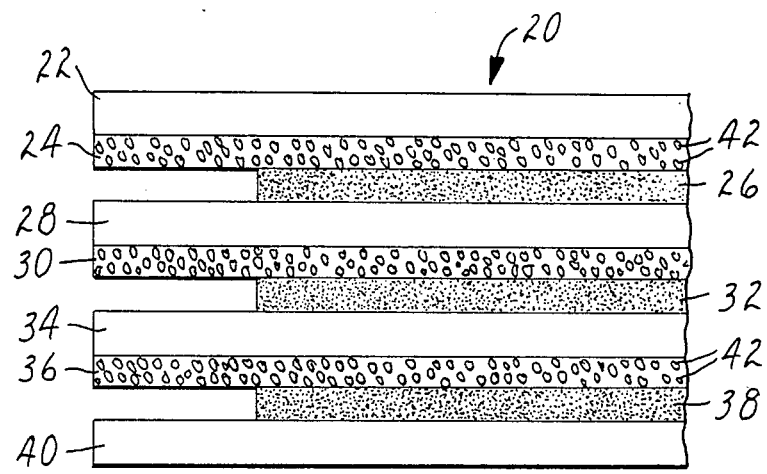
FIG. 2 shows a side view of an alternative construction of a stacked array according to the present invention.

FIG. 2 shows an alternative construction for a stacked array or pad 20 of the present invention. The top sheet 22 has a polymeric binder with microcapsules 42 therein which forms a coating layer 24 on the backside of the top sheet 22. That coating layer 24 is secured by adhesive layer 26 to the next top sheet 28. Similarly, top sheets 28 and 34 are coated on their backsides with microcapsules containing binder layers 30 and 36 and secured to the next top layers by adhesive layers 32 and 38.

DETAILED DESCRIPTION OF THE INVENTION

Existing fragrance releasing elements such as those disclosed in U.S. Pat. No. 4,487,801 are designed to provide a one-time release of material contained therein. After its first use, the article is essentially valueless, although some additional, unbroken capsules in the exposed adhesive may be ruptured by abrasion. The elements are also primarily designed for insertion in magazines or mailers to provide a single occurrence of fragrance.

The present invention provides a pad or stacked array of individual elements. Each individual element, when separated from the pad provides access to the material encapsulated in one of the layers. Each individual element may thereupon be used to provide reasonably accurate and consistant amounts of fragrance to the air or materials for application to other surfaces such as medication, perfumes, lipstick, skin creams, repellant or the like. The pad may be conveniently carried in a pocket or purse with no possibility of spillage of the carried materials. Where the ruptured adhesive layers with microcapsules therein is a hypoallergenic pressure-sensitive adhesive, topical or even transcutaneous medications may be applied by adherence of that layer to the skin.

The present invention relates to an article comprising at least three elements or sheets (and preferably a multiplicity, e.g., 50, 100 or more) each pair of two adjacent elements or sheets being temporarily secured by means of an adhesive layer having microcapsules dispersed therein. The sheet materials or elements of the present invention comprise any sheet or film forming material, or multiple adhered layers of such materials, particularly paper and most preferably coated paper. Generally flexible sheets of paper are preferred although polymeric films may be used. Coated paper is a conventional and standard item in commerce used for printing of quality images thereon. It is generally a fibrous sheet having a pigment-bearing resinous coating on one or both surfaces. Usually the pigment provides a white, bone or ivory coloration to the sheet. Most generally pigments producing a white coloration are used. The binder used in the resinous coating is generally colorless and/or transparent. The binder is generally a synthetic or natural organic polymeric material. Typical pigments for producing white coated paper are fine white pigment such as clay, calcium carbonate, titania, silica, zinc oxide, etc. Typical binders include latices (e.g., styrene-butadiene, butadiene-acrylonitrile, etc.), film-forming polymers (e.g., polymethylmethacrylate), and natural resins (e.g., casein, ammonium caseinate, starch, etc.). The coatings usually comprise between 65-90% by weight of pigment, preferably 70-80% by weight of pigment, and 10-35% by weight of binder, preferably 20-30% by weight of binder.

The adhesive material for the capsules must form a bond to the surfaces of the sheets which is stronger than the cohesive strength of the adhesive with the capsules dispersed therein. Although it is generally desirable to have an adhesive, the absolute cohesive strength of which is less than its adhesive strength to the coated surface of the coated paper cover sheets, this is not essential. When capsules are included within the adhesive composition, the effective cohesive strength of the adhesive tends to be reduced. Adhesives, which by themselves would cause the sheets to be damaged during separation, can be used in combination with capsules in the practice of the present invention because of lowered effective cohesive strength. The capsules in the present invention may comprise any ruptureable capsule containing an active ingredient therein. The tensile rupture strength of the capsules must be such that the cohesive failure of the adhesive results in capsule breakage. It has also been found that the size of the capsules plays a role in the usefulness of capsules within ruptureable sheets according to the practice of the present invention. Generally the capsules should have an average diameter between 6 and 50 microns and preferably between 12 and 30 microns when the capsule payload is between 80 and 90% by weight of the total capsule weight. It is highly preferred that the capsules have an average diameter between 14 and 26 microns and it is most preferred that the capsules have a diameter between 15 and 25 microns. These dimensions play a surprisingly important role in the ability to control the percentage of rupture of capsules in the practice of the present invention. With lower payloads (e.g., 70-80%), the capsules should be larger to provide the necessary rupture strength. The broadest range of capsule size under any conditions would be about 4 to 100 microns, with smaller than 8 micron capsules used with a 90-95% by weight payload. Eight to thirty micron capsules are generally preferred.

A basic relationship exists amongst the factors of peel force adhesive coating weight and the median capsule diameter. This relationship can be expressed as $P = k(Cw/d^2)$, wherein P equals the peel force, Cw equals the adhesive line coating weight, d equals the median diameter of the capsules and k equals a co-efficient relating to binder and substrate properties. The peel force should be in the range of 1.5 to 12 ounces per lineal inch, preferably 1.5 to 8.0 ounces per lineal inch. The coating weight of adhesive and microcapsules should be at a coating weight of approximately one pound for 300 to 800 square feet. Preferably the coating weight should be between approximately one pound for each 400 to 650 square feet. At higher coating weights, the surface of the cover sheets tend to tear, while at lower coating weights, the sheets tend to pull apart and the adhesive to paper bond tends to rupture in advance of the capsules included therein. The capsules should form between 20 and 90 percent by volume of the total adhesive composition, and preferably between 50 and 85 percent of the total composition volume. If certain microcapsule shell materials are used, such as gelatin, the capsule may comprise as much as 100% of the adhesive compositions.

Any class of pressure-sensitive adhesive may be used in the exterior surface of one of said sheets where pressure-sensitive adhesives are used. Typically, acrylate and polyurethane pressure-sensitive adhesives are used to bond the article to another surface.

There are numerous advantages to the practice of the present invention and techniques for improving products using the present invention. The pads may be easily carried in a pocket or purse or suitcase without any fear of spillage. Relatively precise dosages and amounts may be provided without measurement. Samples may be provided without opening sealed containers. Application may be made to surfaces without direct contact by the hands of the person applying the material.

The present invention enables the manufacture of a device for exposing a liquid or spreadable material (e.g., to the atmosphere), said device comprising:
(1) at least three elements or sheets bound by at least two adhesive composition layers,
(2) said adhesive composition microcapsules with said liquid within the shell of said microcapsules, and
(3) said microcapsules having an average diameter between 4 and 100 micrometers, the cohesive strength of the adhesive composition layer being less than the strength of the bond between said adhesive composition and a face of said elements or sheets, the tensile rupture strength of said microcapsules being less than the cohesive strength of the adhesive composition, and the rupture force of said adhesive composition layer containing microcapsules at 50% relative humidity being between at least 1 ounce per linear five-and-one-half inches and less than 45 ounces per linear five-and-one-half inches (greater than 2.0 g/cm and less than 90 g/cm), at least one portion of an interior surface of said sheets having a zone along an edge thereof which is not adhered to an adjacent sheet. It is preferred that the rupture strength between the sheets excedes 8.0 g/cm and is less than 80 g/cm and most preferably excedes 16 g/cm and is less than 75 g/cm. The minimum strength at this ambient condition (i.e., 20° C. and 50% R.H.) is necessary to keep the sheets from falling apart from forces incurred during handling. This problem has frequently occurred in magazine inserts where coated paper was used. The maximum limit on the rupture strength is necessary to keep the paper from tearing (termed fiber pull or fiber rupture) before the adhesive and capsules rupture. This would prevent release of the liquid from the capsules. A "liquid" according to the present invention includes liquids with materials dissolved or dispersed therein (e.g., pigments) and gels which are capable of flowing under moderate pressure. A "spreadable material" means any material which can be spread at room temperature by moderate hand pressure. Soft waxy materials such as lipsticks, rouge and the like are intended by the description. Solid powders, which do not flatten and spread out to form a film-like coating, are not included in the term spreadable. Such materials which are not liquid at room temperature may be cold ground to form particles and then encapsulated. The particles would tend to be rough and irregular in shape, but useful.

It is also desirable to have the construction resist the effects of variable ambient conditions. It is therefore desirable that rupture strength excede 4.0 g/cm after storage at 120° C. and less than 1% R.H. for seventy-two hours. This test would be performed by storage in an oven, removal to a neutral environment (e.g., sealed bag or jar) until the article is at room temperature, and then measuring the rupture strength. It is preferred that the rupture strength is at least 8.0 g/cm and most preferred that the rupture strength is at least 16 g/cm under those conditions. The article must still display a rupture strength between 2 and 90 g/cm at 20° C. and 50% R.H.

A number of methods have been found which enable these conditions to be met according to the present invention. The use of viscosity increasing agents in the binder provides a more even coating and one that ruptures before fiber pull begins. The use of additional coatings over the coated paper which contain polymers different from the binder of the adhesive layer and which do not form a solution or chemically bond to the binder of the adhesive layer provides a useful article according to the present invention. The use of larger size capsules tends to weaken the cohesive strength of the adhesive composite and prevent fiber pull. The use of capsules which are not moisture sensitive in combination with these large capsules (i.e., greater than 30 microns and up to 95 microns) provides a useful adhesive layer. Higher capsule-to-binder ratios reduce the cohesive strength of the adhesive, as does the addition of non-viscosity enhancing particulate fillers.

According to the preferred practice of the present invention, if the stacked array uses coated paper surfaces, the binder between the sheets preferably contains viscosity increasers (viscofiers) in addition to the microcapsules. The use of viscofiers reduced the criticality of proportions of materials and provided increased coating and manufacturing latitude. Viscosity enhancers or viscosity increasing agents are well known in the art. Any material which when present in the coating solution in an amount not greater than 10% by weight increases the viscosity by at least 5% is a viscofier according to the present invention. Preferably viscosity is increased by at least 20%. They are either inorganic particulate materials (e.g., silica, amorphous silica, bentonite clay, montmorillonite clay, etc.) or organic particulate or soluble materials (e.g., water softenable acrylic particles, water swellable poly(methylmethacrylate), water soluble or organic solvent soluble polymers, etc.). The inorganic particles tend to be preferred. The viscofiers enhancers have been found to be necessary in dry weight proportions of the adhesive mix in amounts of from 0.25 to 12% by weight, preferably from 5 to 12% by weight. In general, the weight proportions of materials in the dried adhesive layers according to the present invention are generally as follows:

Microcapsules: 21–80%
Adhesive: 19.75–70%
Viscosity Enhancers: 0.25–12%

Other optional ingredients such as surfactants, coating aids and the like may be present. Preferred proportions of these ingredients are:

Microcapsules: 44.5–80%
Adhesive: 19.5–55%
Viscosity Enhancers: 0.5–10%

The nature and composition of the adhesive binder is not critical to the practice of the invention as long as the required adhesive and cohesive properties are met. The adhesive may be pressure sensitive, water or solvent soluble or thermally activatable. A single layer of a non-pressure-sensitive adhesive is preferred. There is no need for rejoining the sheets after rupturing of the capsules and so the pressure sensitive function is not essential to practice of the invention although it is highly desirable in some uses as previously described.

The adhesive (with microcapsules) may be applied between two separate sheets in either a continuous or discontinuous patterns. It is usually desirable to leave at least some portion of at least one outer edge of the sheets unbonded so as to provide an area where separation can be easily started.

It is preferred that the capsule-bearing adhesive coated inside portion between the sheets constitute from 60 to 95% of the surface area of the sheets. 10 to 95 percent adhesive coverage can be used to leave an edge or corner that can be readily grasped to pull one sheet from another. Some uses may allow for only a single corner to be uncoated so as to provide a starting point for the separation of the sheets, but the 60 to 95% range is preferred with 70 to 90% more preferred. The adhesive free zones may be on the same edge of the sheet or may be on varying or alternative edges of the sheet (e.g., left side, then right side, then left again).

Any class of adhesives including but not limited to polyurethanes, polyacrylates, polyvinyl resins (e.g., polyvinyl alcohol, polyvinyl chloride), polyamides, polyesters, polyolefins, starches, gum arabic, gelatin and the like may be readily used in the practice of the present invention. Washing of the capsules before mixing them with the adhesive often tends to provide more consistency in their properties by removing low molecular weight, unreacted materials.

In effect, to best practice the present invention it is desirable that certain properties within the article have relative values for each of the materials used. The cohesive strength of the sheet material should exceed the adhesive strength between the binder and the sheet. The adhesive strength of the binder to the sheet should exceed the cohesive strength of the binder and capsules therein. The cohesive strength of the binder should exceed the tensile rupture limits of the capsules. As previously noted, the size of the capsules has an important effect upon the practice of the present invention. With capsules less than 8 microns, there tends to be less rupturing of the capsules during separation of the sheets which prevents the useful and efficient release of materials. Above 30 microns, the particles are so large that they are more readily burst (sometimes too readily) by handling of the sheets and manufacturing procedures. Furthermore, with the large size particles it is extremely difficult to control bursting upon separation of the sheets because of increased effects upon adhesive and cohesive properties of materials in contact with the capsules. The preferred ranges of 8 to 30 and 15 to 25 microns is important to the practice of the present invention with a high quality product. Within these limits, rupture in excess of 50 percent of the capsules can be easily obtained. Rupture in excess of 80 percent of the capsules can often be accomplished in the practice of the present invention within those limits.

The capsules may contain a wide variety of active materials therein. The least useful of materials to be included therein would be coloring agents since separation of the sheets would generally produce uniform coloration rather than a distinct image. The most preferred types of ingredients would be fragrant materials (such as essences and perfumes) or materials which provide chemically active vapors or liquids (e.g., bacteriostats, insect repellants or deodorants) to be wiped on or transferred to another surface. These may or may not also be colored. For example, a testing kit for the presence of chemical vapors could be produced by providing material within the capsules which would react in the vapor phase with the material for which a leak is being investigated. By separating the sheet, rupturing the capsules and exposing the vapor test material, a color forming reaction in the air or on the sheet could be readily observable.

These and other aspects of the present invention will be shown in the following examples.

EXAMPLE 1

A 70 lb stock of one side coated paper was used as the top sheet 2 of the label 14. A slurry was prepared from rose fragrance in urea-aldehyde microcapsules manufactured according to the process of Example 10 of U.S. Pat. No. 3,516,941. The slurry contained 64% dry weight of capsules, 24.50% dry weight of poly(vinyl alcohol) (Gelvatol ® 40-10), 10.50% poly(vinyl alcohol) (Gelvatol ® 20-60), and 1% glycerin in water. The slurry was applied to 85% of the surface of the uncoated face of a continuous web of pressure sensitive label stock at a coating weight of 3.5 pounds per 1300 ft². After the slurry was applied, the uncoated face of the top sheet was mated to the wet slurry coated face of the label stock and dried. The laminate was then die-cut into appropriate sizes (e.g., 3×8 cm). The cut labels were then removed and affixed by the pressure sensitive-adhesive to one another in a stacked array of fifty individual elements. The edge of the top sheet which was over the uncoated surface of the label stock was easily raised and grasped by one hand. Upon pulling the top sheet, fragrance was released and the bottom sheet remained firmly adhered to the remaining elements of the pad.

Mechanical handling of the pad did not produce any significant level of capsule breakage.

EXAMPLE 2

The slurry of Example 1 was coated onto 85% of the surface of the coated face of one-side coated paper stock at a coating weight of 3.5 pounds per 1300 ft². Before drying, another sheet of paper stock was laid coated side up on the slurry coated surface. The application of slurry and paper stock was repeated until fifty sheets were arrayed. The pad was oven dried at moderate temperatures (about 110° F., 42° C.) for twelve hours, then die-cut into pads that were 3×8 cm. Individual elements could be stripped from the pads. The adhesive bearing surface of the element was rubbed against the skin, transferring the fragrance.

I claim:

1. A stacked, coherent array of elements for providing access to an encapsulated liquid or spreadable material, said array comprising
    (1) at least three sheets, each pair of adjacent sheets in adjacent elements bound by an adhesive composition layer,
    (2) said adhesive composition layer containing microcapsules with an encapsulated material comprising a liquid or spreadable material within the shell of the microcapsules, and
    (3) said microcapsules having an average diameter between 4 and 100 micrometers,
the cohesive strength of the adhesive composition layer being less than the strength of the bond between said adhesive composition and the faces of said sheets, the tensile rupture strength of said microcapsules being such that the cohesive failure of the adhesive results in breakage of the microcapsules, and the tensile rupture strength between said two sheets being at least 1.0 g/cm and less than 90 g/cm at 20° C. and 50% relative humidity.

2. The device of claim 1 wherein said adhesive composition comprises said microcapsules and a polymeric binder, and there are at least twenty adjacent pairs of 3. The device of claim 2 wherein said surfaces are on flexible sheets of paper and said polymeric binder is a pressure-sensitive adhesive.

4. The device of claim 2 wherein said sheets are flexible paper and said binder is a non-pressure-sensitive polymeric binder.

5. The device of claim 4 wherein said individual elements comprise two sheets, a top sheet and a bottom sheet, having said adhesive composition layer between said two sheets and also having a pressure-sensitive adhesive layer on the surface of said bottom sheet which is not in contact with said adhesive composition layer.

6. The device of claim 5 wherein said encapsulated material is a liquid which comprises a perfume.

7. The device of claim 5 wherein said encapsulated material is a liquid which comprises a medically active material.

8. The device of claim 5 wherein said encapsulated material is a spreadable material selected from the group consisting of lipstick, rouge, and medically active ingredients.

9. The device of claim 4 wherein said microcapsules comprise between 50 and 85% by volume of said adhesive composition and are formed of a urea-aldehyde polymer.

10. The device of claim 2 wherein said microcapsules comprise gelatin and are between 21 and 100% by weight of said adhesive composition and said binder comprises between 0 and 78.75% by weight.

11. The device of claim 2 wherein said microcapsules comprise between 50 and 85% by volume of adhesive composition and comprise a polymeric shell material.

12. The device of claim 2 wherein said encapsulated material is a liquid which comprises a perfume and the shell of said microcapsule comprises a urea-formaldehyde resin.

13. The device of claim 2 wherein said encapsulated material is a liquid which contains a medically active ingredient.

14. The device of claim 2 wherein said encapsulated material is a spreadable material selected from the group consisting of lipstick, rouge, and medically active ingredients.

15. The device of claim 1 wherein said microcapsules have an average diameter between 8 and 30 micrometers.

16. The device of claim 1 wherein said individual elements comprise two sheets, a top sheet and a bottom sheet, having said adhesive composition layer between said two sheets and also having a pressure-sensitive adhesive layer on the surface of said bottom sheet which is not in contact with said adhesive composition layer.

17. The device of claim 16 wherein said encapsulated material is a liquid which comprises a perfume.

18. The device of claim 1 wherein said top sheet has perforated lines thereon to enable removal of individual portions of said top sheet.

19. The device of claim 1 wherein the encapsulated material is a liquid which contains a medically active ingredient.

20. The device of claim 1 wherein said encapsulated material is a spreadable material selected from the group consisting of lipstick, rouge, and medically active ingredients.

* * * * *